United States Patent
Lee

(10) Patent No.: US 9,888,982 B2
(45) Date of Patent: Feb. 13, 2018

(54) DEVICE FOR GENERATING DATA ON CLEAR ALIGNER

(71) Applicant: Jinkyun Lee, Seoul (KR)

(72) Inventor: Jinkyun Lee, Seoul (KR)

( * ) Notice: Subject to any disclaimer, the term of this patent is extended or adjusted under 35 U.S.C. 154(b) by 0 days.

(21) Appl. No.: 14/936,476

(22) Filed: Nov. 9, 2015

(65) Prior Publication Data

US 2016/0157961 A1  Jun. 9, 2016

(30) Foreign Application Priority Data

Dec. 5, 2014  (KR) .................. 10-2014-0174386

(51) Int. Cl.
| | |
|---|---|
| *G06K 9/00* | (2006.01) |
| *A61C 7/00* | (2006.01) |
| *A61C 13/00* | (2006.01) |
| *A61C 7/08* | (2006.01) |
| *A61C 8/00* | (2006.01) |
| *G06T 7/00* | (2017.01) |
| *A61C 19/06* | (2006.01) |
| *A61C 7/36* | (2006.01) |

(52) U.S. Cl.
CPC ............. *A61C 7/002* (2013.01); *A61C 7/00* (2013.01); *A61C 7/08* (2013.01); *A61C 8/0096* (2013.01); *A61C 13/0004* (2013.01); *G06T 7/0012* (2013.01); *A61C 7/36* (2013.01); *A61C 19/063* (2013.01); *G06T 2207/10081* (2013.01); *G06T 2207/30036* (2013.01)

(58) Field of Classification Search
CPC ............ G06T 2207/30036; G06T 2207/10081
See application file for complete search history.

(56) References Cited

U.S. PATENT DOCUMENTS

2008/0248443 A1* 10/2008 Chishti ................. A61C 7/00
  433/24
2009/0117507 A1  5/2009 Abolfathi et al.
(Continued)

FOREIGN PATENT DOCUMENTS

| EP | 2 581 062 | 4/2013 |
|---|---|---|
| JP | 2012-096052 | 5/2012 |

(Continued)

OTHER PUBLICATIONS

European Search Report for EP 15194794.2, dated Jul. 5, 2016, 14 pages.

(Continued)

*Primary Examiner* — Oneal R Mistry
(74) *Attorney, Agent, or Firm* — Morrison & Foerster LLP

(57) ABSTRACT

Provided is a device for generating data on a clear aligner, which is equipped with a module for generating the data on the clear aligner, which generates 3D data relating to the clear aligner, the module including; a first module that receives data on a current dental state from a scanning apparatus that scans patient's teeth; a second module that generates 3D data on a state of the patient's teeth and of the vicinity of the patient's teeth based on data that results from the scanning a third module that generates data relating to a 3D clear aligner with a predetermined thickness; and a fourth module that processes the data relating to the 3D clear aligner in such a manner that at least one of a shape and a feature of the 3D clear aligner is changed.

12 Claims, 7 Drawing Sheets

(56) References Cited

U.S. PATENT DOCUMENTS

| | | | |
|---|---|---|---|
| 2009/0191503 A1* | 7/2009 | Matov | A61C 7/00 433/24 |
| 2009/0291407 A1* | 11/2009 | Kuo | A61C 1/084 433/24 |
| 2009/0311645 A1 | 12/2009 | Matty et al. | |
| 2011/0207072 A1* | 8/2011 | Schiemann | A61C 7/002 433/9 |
| 2013/0095446 A1 | 4/2013 | Andreiko et al. | |
| 2014/0178829 A1 | 6/2014 | Kim | |
| 2015/0305669 A1* | 10/2015 | Hultgren | A61B 5/4547 433/27 |

FOREIGN PATENT DOCUMENTS

| | | |
|---|---|---|
| KR | 10-2006-0079441 | 7/2006 |
| KR | 10-1349356 | 1/2014 |
| KR | 10-1463424 | 11/2014 |
| WO | WO-2011/143620 | 11/2011 |

OTHER PUBLICATIONS

Partial European Search Report for EP 15194794.2, dated Apr. 13, 2016, 8 pages.

* cited by examiner

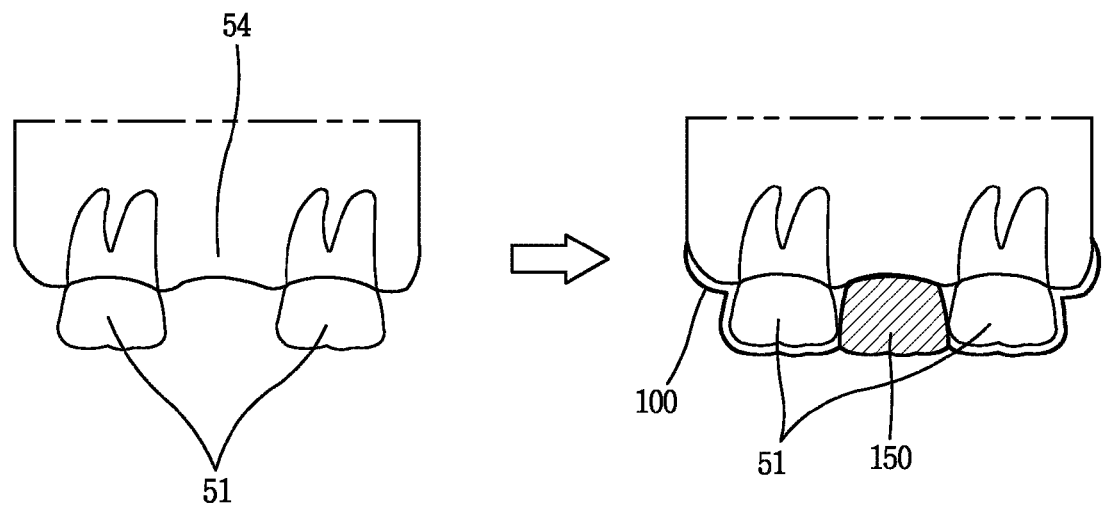
FIG. 11
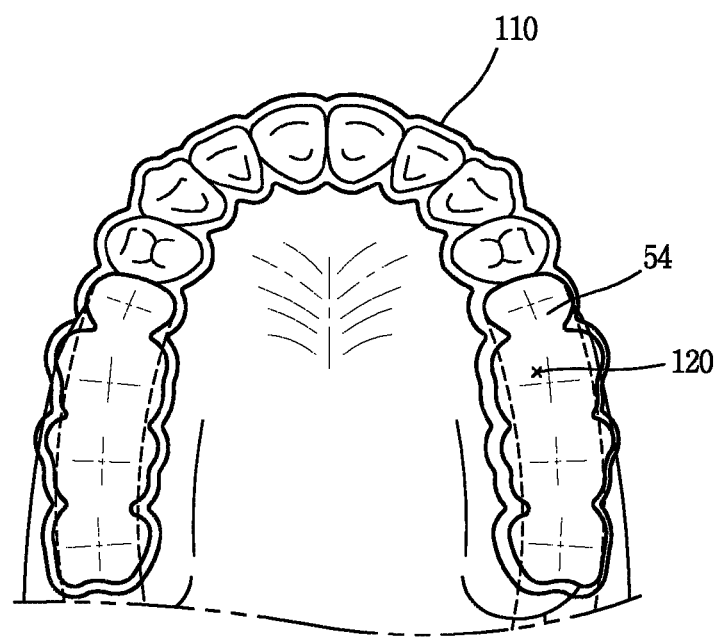

DEVICE FOR GENERATING DATA ON CLEAR ALIGNER

CROSS-REFERENCE TO RELATED APPLICATIONS

Pursuant to 35 U.S.C. § 119(a), this application claims the benefit of earlier filing date and right of priority to Korean Application No. 10-2014-0174386, filed on Dec. 5, 2014, the contents of which is incorporated by reference herein in its entirety.

BACKGROUND OF THE INVENTION

1. Field of the Invention

The present invention relates to a device for generating aligner data using dental data that is obtained using a CT apparatus.

Generally, a dental alignment method is categorized into a dental alignment method that uses a metal alignment device, a lingual-side alignment method in which an aligner is placed in an oral cavity, and a transparency alignment method in which a clear aligner made of clear material is attached to teeth for dental alignment.

Particularly, the clear alignment method is one in which the clear aligner made of clear material covers teeth. In this method, the aligner is not seen from the outside and is detachably attached to the teeth. Thus, the method is gaining popularity due to its comfortability when compared to other alignment methods.

However, in the clear alignment method in the related art, in a case where there is a dentist's request to manufacture a clear aligner, a device for generating data on an alignment target tooth generates data on an arrangement of multiple alignment target teeth that are involved in dental movement, from dental data on a patient that results from 3D-scanning by an 3D scanner. Then, a cast of the teeth is formed by 3D-printing the generated data on the alignment target tooth, and the clear aligner that is capable of performing dental alignment in multiple stages is manufactured by pressing clear films against the cast of the teeth using a PET sheet.

At this point, the device for generating data on an alignment target tooth needs to manipulate the dental data on the patient in such a manner that the teeth are separated from each other at a real-world separation distance between the teeth in a real-world shape to move the tooth for the alignment, but the data manipulation for the precise separation of the teeth is impossible. Thus, an error occurs when the data the alignment target tooth is generated.

In addition, in a case where the aligner is manufactured using the dental data, an opening is manually formed in the aligner or a protrusion portion is manually formed on the aligner, whenever necessary. In some cases, it is difficult to form the opening and the protrusion portion in and on an intended portion of the aligner. In addition, it is also difficult to form the opening and the protrusion in and on some portions of the aligner. In addition, although manufactured according to the same specification, the aligner differs in terms shapes and position of the opening and the protrusion portion.

To solve this problem, a device is considered that makes an amendment to the aligner data.

SUMMARY OF THE INVENTION

Therefore, an aspect of the detailed description is to provide to provide a device for generating data on a clear aligner, which generates aligner data based on dental data.

Another aspect of the detailed description is to provide a device for generating data on a clear aligner, which is capable of changing shape- or attribute-related data on a clear aligner, considering a patient's situation.

Still another aspect of the detailed description is to simplify an existing method of manufacturing a clear aligner, which includes many steps, and to remove a difference in position and size between the clear aligners that results from manual forming of an opening in and a protrusion on clear aligner, thereby shortening the time taken for alignment of a tooth using the aligner.

To achieve these and other advantages and in accordance with the purpose of this specification, as embodied and broadly described herein, there is provided a device for generating data on a clear aligner, which is equipped with a module for generating the data on the clear aligner, which generates 3D data relating to the clear aligner based on 3D data that contains data on a current arrangement of patent's teeth and on a gingival internal structure, the module; a first module that receives data on a current dental state from a scanning apparatus that scans patient's teeth; a second module that generates 3D data on a state of the patient's teeth and of the vicinity of the patient's teeth based on data that results from the scanning a third module that generates data relating to a 3D clear aligner with a predetermined thickness; and a fourth module that processes the data relating to the 3D clear aligner in such a manner that at least one of a shape and a feature of the 3D clear aligner is changed.

In the device according to the aspect of the present invention, the third module may adjust a thickness attribute among attributes of the data on the 3D clear aligner.

In the device according to the aspect of the present invention, the third module may individually adjust thicknesses of the 3D clear aligner in a database, which correspond to teeth that are expressed in the 3D dental data, respectively.

In the device according to the aspect of the present invention, the fourth module may form a button member, which an elastic member applying pressure to a tooth is locked onto, on the 3D clear aligner, in such a manner that the tooth is gradually moved into a gingiva or is gradually moved out of the gingiva.

In the device according to the aspect of the present invention, the fourth module may form a groove portion in one portion of the 3D clear aligner in such a manner that the 3D clear aligner has an opening.

In the device according to the aspect of the present invention, in a case where the elastic member is locked onto the button member, at least one portion of the elastic member may pass through the groove portion.

In the device according to the aspect of the present invention, the groove may be formed in an upper portion of an empty space in such a manner that a virtual position of an artificial implant tooth is guided.

In the device according to the aspect of the present invention, the fourth module may form a protrusion portion that protrudes toward a tooth that needs alignment, from an inside surface of the 3D clear aligner, in such a manner that pressure is applied to the tooth in an intended direction.

In the device according to the aspect of the present invention, the fourth module may form the 3D clear aligner, in such a manner that the 3D clear aligner is positioned a given distance away from the 3D tooth so that a space into which medical stuff is introduced is formed in the 3D clear aligner.

In the device according to the aspect of the present invention, in a case where the 3D dental data of the patient whose tooth is extracted is available, the fourth module may form the 3D clear aligner in such a manner that the 3D clear aligner further includes a dummy tooth in the form of an artificial tooth that is to be implanted into a space which corresponds to the extracted tooth.

In the device according to the aspect of the present invention, the fourth module may form the 3D clear aligner in such a manner that the 3D clear aligner has multiple layers that are laminated on each other.

In the device according to the aspect of the present invention, the multiples may include a first layer and a second layer, the first layer may be formed to cover the 3D teeth, and the second layer, which has a different color than the first layer, may be formed to cover the first layer and to be subject to wear due to an external force.

In the device according to the aspect of the present invention, the fourth module may form a 3D clear aligner that corresponds to an above-teeth portion of a patient's upper jaw and a 3D clear aligner that corresponds to a below-teeth portion of the patient's lower jaw, in such a manner that the 3D clear aligner that corresponds to the above-teeth portion is greater in thickness than the 3D clear aligner that corresponds to the below-teeth portion.

In the device according to the aspect of the present invention, the fourth module may form at least one portion of the 3D clear aligner that is made of different material.

In the device according to the aspect of the present invention, the fourth module may indicate an image or a character on the 3D clear aligner.

In the device according to the aspect of the present invention, the fifth module may be a 3D printer.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWINGS

The accompanying drawings, which are included to provide a further understanding of the disclosure and are incorporated in and constitute a part of this specification, illustrate exemplary embodiments and together with the description serve to explain the principles of the disclosure.

FIG. 10 is a conventional diagram illustrating the clear aligner that further includes a dummy tooth in the form of an artificial teeth in an empty space between teeth; and FIG. 11 illustrates a groove portion that is formed in an upper portion of the empty space for the artificial tooth in such a manner that a position of a portion of a gingiva into which the artificial tooth is implanted is guided for an operation for implant.

DETAILED DESCRIPTION OF THE INVENTION

Description will now be given in detail of the exemplary embodiments, with reference to the accompanying drawings. For the sake of brief description with reference to the drawings, the same or equivalent components will be provided with the same reference numbers, and description thereof will not be repeated.

Figure 1:
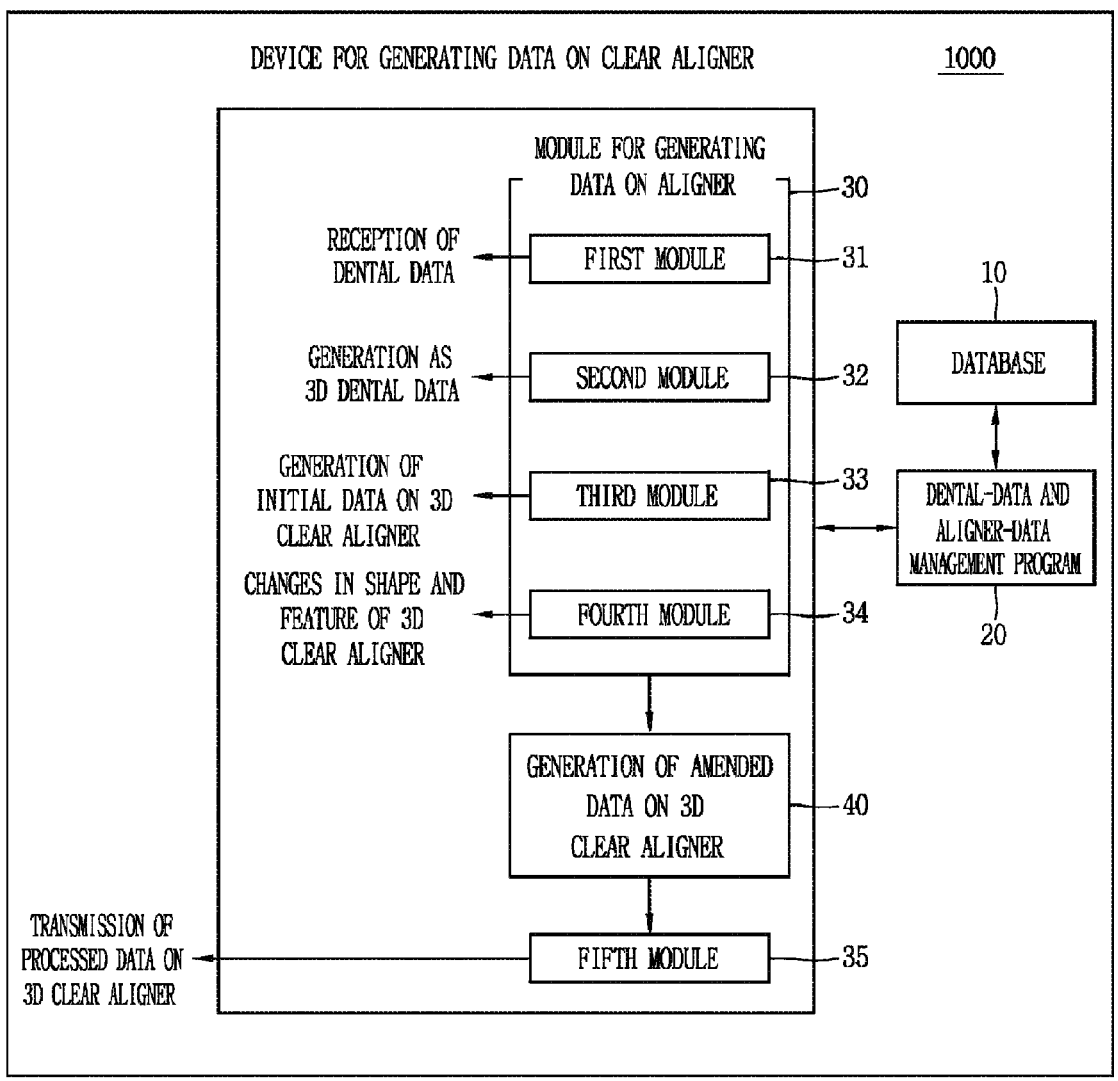
FIG. 1 is a systematic configuration diagram that schematically illustrates a device 1000 for generating data on a clear aligner according to one embodiment of the present invention.

FIG. 1 is a systematic configuration diagram that schematically illustrates a device 1000 for generating data on a clear aligner according to one embodiment of the present invention.

The device 1000 for generating data on a clear aligner is a device that generates data on a clear aligner 100 in multiple steps, based on a current arrangement of patent's teeth.

The device 1000 for generating data on a clear aligner is configured to include a database 10, a dental-data and aligner-data management program 20, an aligner data generation module 30, and a module for generating amended data on a 3D clear aligner 100.

Pieces of aligner data that are generated, such as pieces of pre-amendment and post-amendment contour data on and pieces of guide information on the aligner, are stored and managed in the database 10.

Interfaces between functions of units and modules of the device 1000 for generating data on a clear aligner are provided by the dental-data and aligner-data management program 20.

The device 1000 for generating data on a clear aligner includes the aligner data generation module 30 that generates the aligner data. A process will be described below in which the aligner data generation module 30 preprocesses the aligner data for generating the aligner data.

The device 1000 for generating data on a clear aligner includes the aligner data generation module 30 for the clear aligner 100, which generates 3D data relating to the clear aligner 100, based on 3D data that contains data on a current arrangement of patent's teeth and on a gingival internal structure.

The aligner data generation module 30 for the clear aligner 100 includes first to fourth modules 31, 32, 33, and 34.

The first module 31 receives data on a current dental state from a scanning apparatus that scans patent's teeth. The scanning apparatus here may be an apparatus that is capable of recognizing the patent' teeth in a 3D manner. For example, the scanning apparatus may be a fan beam computed tomography (fan beam CT) apparatus, a con beam computed tomography (cone beam CT) apparatus, a panoramic X-ray (panoramic radiograph) apparatus, or a 3D scanner. In a case of the cone beam CT apparatus, there is a likelihood that information relating to the patent' teeth will not be obtained. Thus, as a supplement to data that is received from the cone beam CT apparatus, data that results from modelling a plaster cast of the patent's oral cavity is included.

The second module 32 generates 3D data on a state of the patent's teeth and of the vicinity of the patent's teeth, based on the data that results from the scanning. That is, the 3D data on the state of the patent's teeth and of the vicinity of the patent's teeth is generated based on the data that results from the fan beam CT apparatus, the cone beam apparatus, the panoramic X-ray apparatus, or the 3D scanner, and on data that results from scanning the plaster cast of the oral cavity. Desirably, the teeth and of the vicinity of the teeth include a crown, a dental root, a gingiva, and an alveolar bone.

The third module 33 generates data relating to the 3D clear aligner 100 with a predetermined thickness, which is formed to enclose a surface of the tooth that is expressed in a 3D manner.

For example, the data on the 3D clear aligner 100 is generated which has the predetermined thick in such a manner as to cover the surface of the tooth that is expressed in a 3D manner. Then, if the dental data is deleted, only the data on the 3D clear aligner 100 remains. Furthermore, after the tooth that is expressed in a 3D manner is moved, it is possible to generate the data on the 3D clear aligner 100. Thus, for dental alignment, it is possible to edit a less amount of the data on the 3D clear aligner 100.

The fourth module 34 processes the data on the 3D clear aligner 100 in such a manner that at least one of a shape and a feature of the 3D clear aligner 100 is changed.

For example, the clear aligner 100 is changed in such a manner that its thickness is increased or decreased. Alternatively, the clear aligner 100 is changed in such a manner that its elasticity differs from one tooth to another.

The device 1000 for generating data on a clear aligner may further include a fifth module 35 that transmits the processed data on the 3D clear aligner 100, which is the data on the 3D clear aligner 100 that is amended and generated by the fourth module 34 due to a change in at least one of the shape and the feature of the clear aligner 100, to an aligner manufacturing apparatus.

The data on the 3D clear aligner 100 that is transmitted through the fifth module 35 is used by the aligner manufacturing apparatus to manufacture the clear aligner 100. Then, the fifth module 35 may be a 3D printer. The clear aligner 100 can be manufactured using the 3D printer.

Figure 2A:
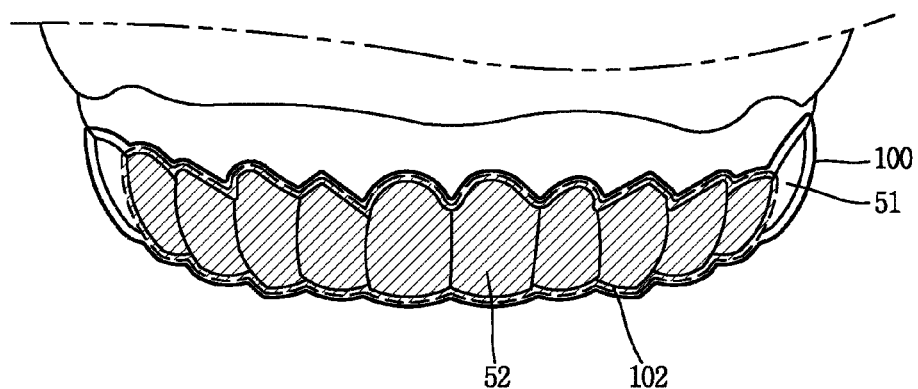
FIGS. 2A and 2B are diagrams illustrating a clear aligning device in which a space into which medical stuff is introduced is formed, according to one embodiment of the present invention.
Figure 2B:
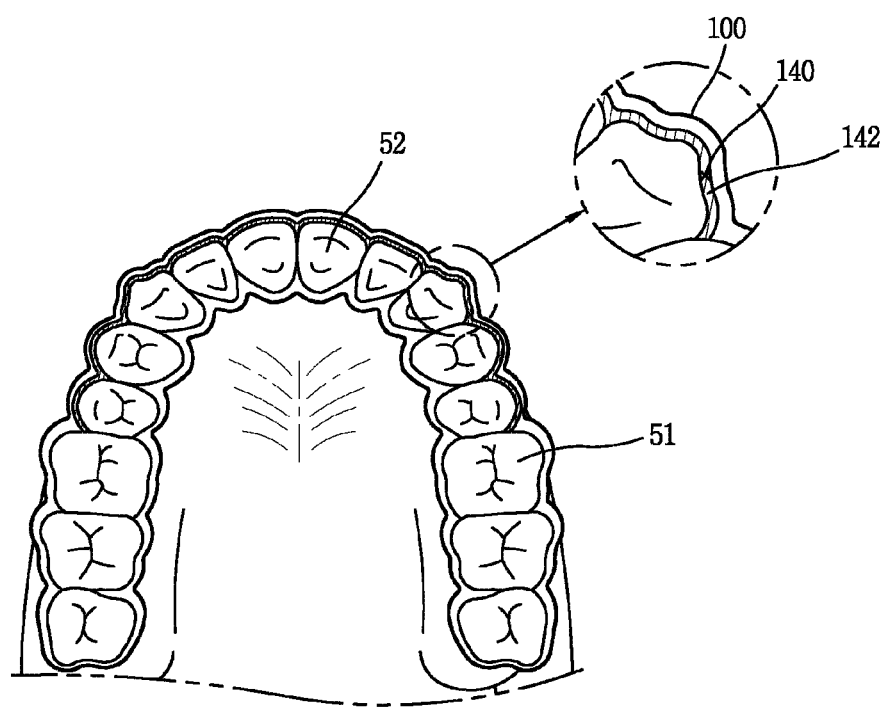

FIGS. 2A and 2B are diagrams illustrating a clear aligning device in which a space into which medical stuff is introduced is formed, according to one embodiment of the present invention.

The third module 33 can adjust a thickness attribute among attributes of the data on the 3D clear aligner 100. The thickness of the 3D clear aligner 100 comes in three or more types: a soft type, a medium type, and a hard type. With this change in the thickness, in a case where the patient wears the aligner, an amount of alignment can be determined and the amount of alignment can be adjusted.

In addition, the third module 33 can individually adjusts thicknesses of the 3D clear aligner 100 in a database, which correspond to the teeth that are expressed in the 3D dental data, respectively.

The teeth that have different amounts of movement can be moved in a uniform manner by adjusting the thicknesses of the 3D clear aligner 100 that correspond to these tooth, receptively.

Then, the fourth module 34 forms the space into which the medical stuff is introduced, in the 3D clear aligner 100. To do this, the 3D clear aligner 100 is formed in such a manner that the 3D clear aligner 100 is positioned a predetermined distance from 3D teeth. A medical stuff tray portion 140, that is, the space into which the medical stuff is introduced, is formed by forming the 3D clear aligner 100 a given distance from the 3D clear aligner 100.

Medical stuff 142 for tooth-lightening is applied to the internal surface of the medical stuff tray portion 140. The patent wears the clear aligner 100 to which the medical stuff 142 is applied, and thus can achieve the dental alignment and the tooth-lightening at the same time.

A tooth 52 that need lightening may be one that is generally arranged to the front side and thus can be easily seen from the outside. Therefore, the medical stuff tray portion 140 is placed in such a manner as to enclose the teeth that are arranged to the front side. In addition, the medical stuff tray portion 140 is desirably placed at a distance of approximately 0.3 mm to 1.5 mm from the teeth.

Figure 3:
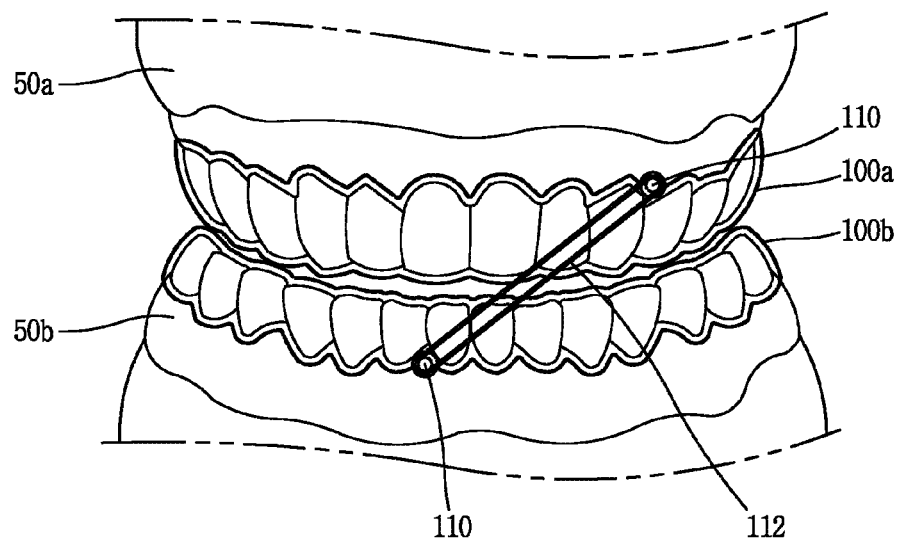
FIG. 3 is a diagram illustrating the clear aligning device that aligns teeth using a button member and an elastic member, according to one embodiment of the present invention.

FIG. 3 is a diagram illustrating the clear aligning device that aligns the teeth using a button member 110 and an elastic member 112, according to one embodiment of the present invention.

The fourth module can form the button member 110, which the elastic member 112 applying pressure to a tooth is locked onto, on the 3D clear aligner 100. At this point, two or more button members 110 may be formed. This is done to lock the elastic member 112 onto the two or more button members 110, and thus to produce a compression force that is exerted on the two or more button members 110.

Referring to the drawings, two end portions of the elastic member 112 are formed to be locked onto the button member 110 that is formed on a clear aligner 100a which corresponds to an above-teeth portion 50a of a patient's upper jaw and the button member 110 that is formed on a clear aligner 100b which corresponds to an below-teeth portion 50 b of a patient's lower jaw, respectively, in order to exert an elastic force on the two portions.

Then, the fourth module can form the 3D clear aligner 100 in such a manner that the 3D clear aligner 100 has multiple layers which are laminated on each other. The multiple layers includes a first layer and a second layer. The first layer is formed to cover the 3D teeth. The second layer, which has a different color than the first layer, is formed to cover the first layer and to be subject to wear due to an external force.

The first layer and the second layer are formed to adhere closely to each other.

Thus, when the patient grinds his/her teeth while he/she sleeps wearing the aligner, with this teeth-grinding motion, it is possible to know which teeth he/she grinds. With the clear aligner 100, it is possible to know which teeth the patient grinds and a pattern in which the patient grinds his/her teeth.

Then, the fourth module can form a 3D clear aligner 100a that corresponds to the above-teeth portion of the patient's upper jaw, and a 3D clear aligner 100b that corresponds to the below-teeth portion of the patient's lower jaw, in such a manner that the 3D clear aligner 100b are greater in thickness than the 3D clear aligner 100b. The increase in the thickness of the 3D clear aligner 100b corresponding to the lower jaw makes it possible for the 3D clear aligner 100b corresponding to the lower jaw to serves as a splinter that protects a temporomandibular joint. Then, the patient usually wears the 3D clear aligner 100b with a normal thickness, but wears the 3D clear aligner 100b with a relatively-thicker 3D clear aligner 100b while asleep. Thus, the 3D clear aligner 100b serves as the splinter.

In addition, the fourth module can form at least one portion of the 3D clear aligner 100 that is made of different material. Thus, an amount of alignment is determined relatively depending on which material a portion of the 3D clear aligner is made of. For example, when a tooth that needs an large amount of alignment and a toot that needs a small amount of alignment are adjacent to each other, a portion of the 3D clear aligner 100 that is made of low-elastic material is used for the tooth that needs the small amount of alignment, and a portion of the 3D clear aligner 100 that is made of high-elastic material is used for the tooth that needs the large amount of alignment. Thus, the tooth that needs the large amount of alignment and the tooth that needs the small amount of alignment can be suppressed, to the maximum possible, from being moved together.

Then, the fourth module can indicate an image or a character on the 3D clear aligner 100. Thus, a name of the patient, information indicating which of the upper jaw and the lower jaw the aligner is used for, the order in which the device is provided according to the extent to which the alignment progresses, and the like are described on the clear aligner 100.

Figure 4:
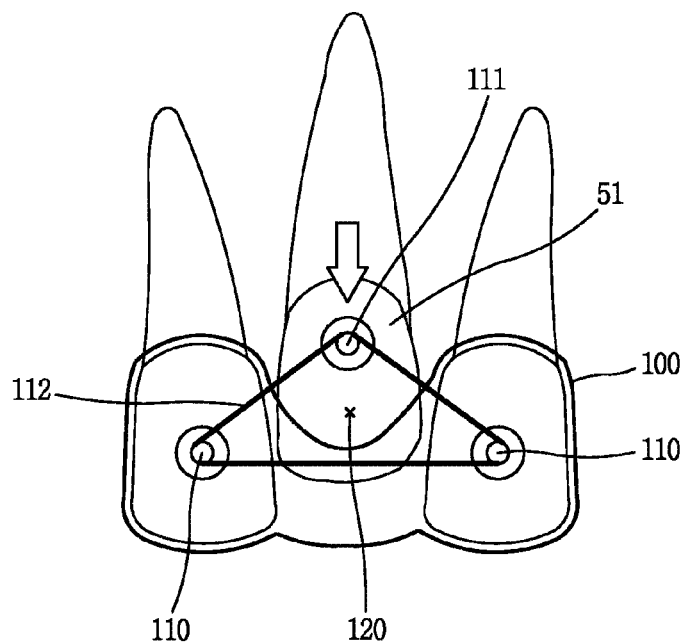
FIG. 4 is a conceptual diagram illustrating that a tooth is gradually moved out of a gingiva using the button member and the elastic member.

FIG. 4 is a conceptual diagram illustrating that a tooth is gradually moved out of the gingiva using the button member 110 and the elastic member 112.

The fourth module can form a groove portion 120 in one portion of the 3D clear aligner 100, in such a manner that the 3D clear aligner 100 has an opening. At least one portion of a tooth 51 is exposed, through the groove portion 120, to the outside at the surface of the aligner.

Referring to the drawings, the groove portion 120 is formed in the aligner in such a manner that the groove portion 120 is positioned far away from the end portion of the tooth 51. This is done to expose one portion of the tooth 51 to the outside. The tooth that is positioned more inward toward the gingiva than the adjacent tooth 51 is exposed, through the groove portion 120, to the outside.

The button member 110 is formed on the tooth that is exposed through the groove portion 120. Then, two button members 110 are formed in the aligner in such a manner that the two button members 110 are positioned to the both sides of the button member 110 that is formed on the tooth, respectively. The elastic member 112 is locked onto the three button members 110 that are formed on the tooth and the aligner. The elastic member 112 applies pressure to the tooth 51 toward the end portion of the tooth 51. Thus, the tooth 51 is gradually moved outward from its current position. Furthermore, the more the tooth 51 is moved outward, the shorter a distance between the button member 110 formed on the tooth 51 and the button member 110 formed on the aligner becomes. This reduces an amount of force that is exerted on the tooth 51.

Figure 5A:
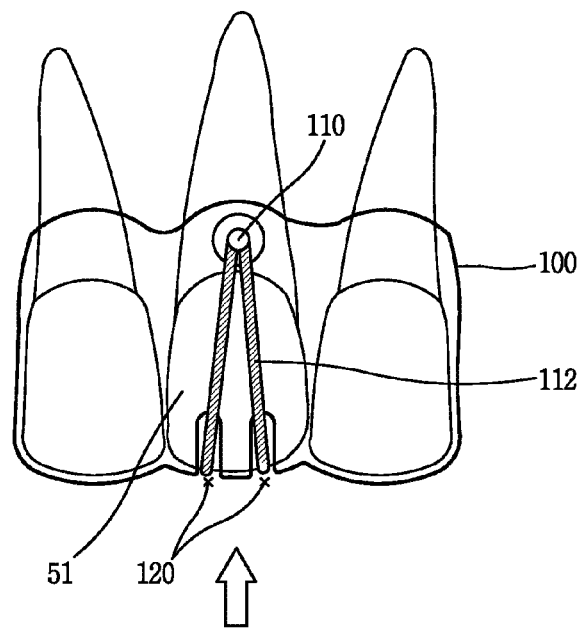
FIGS. 5A, 5B, and 5C are conventional diagrams each of which illustrates that a tooth is gradually moved into the gingiva using the button member and the elastic member.
Figure 5B:
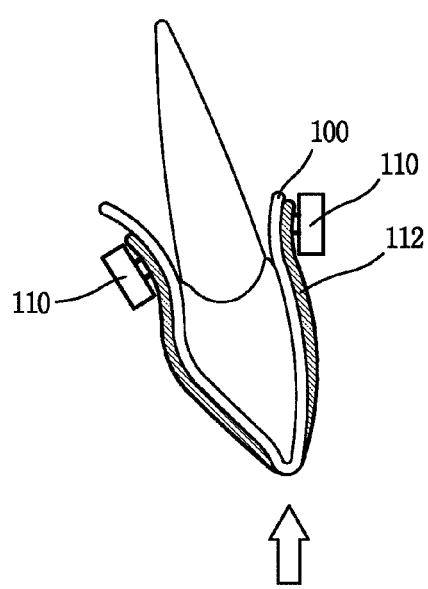
Figure 5C:
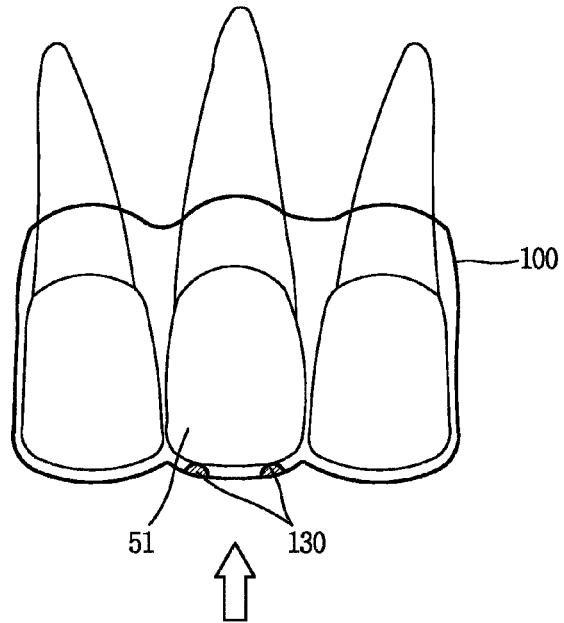

FIGS. 5A, 5B, and 5C are conventional diagrams each of which illustrates that a tooth is gradually moved into the gingiva using the button member 110 and the elastic member 112.

In a case where the elastic member 112 is locked onto the button member 110, the groove portion 120 is formed in such a manner that at least one portion of the elastic member 112 passes through the groove portion 120.

Referring to FIGS. 5A and 5B, the button member 110 is formed on the front surface and the rear surface of the aligner. Then, the groove portion 120 is formed on the end portion of the aligner. The groove portion 120 is formed in a recessed manner in such a manner that the groove portion 120 is positioned a given distance from the end portion of the tooth 51 that has to be moved inward toward the gingiva.

In order to apply pressure to the tooth 51, the elastic member 112 is locked onto the button members 110 that are formed on the front surface and the rear surface of the aligner, and the elastic member 112 passes through the aligner through the groove portion 120 that is formed in the end portion of the aligner. Thus, the pressure is applied to the tooth 51 from the end portion of the tooth 51 inward toward the gingiva. Thus, the tooth 51 is gradually moved into the gingiva.

In addition, as illustrated in FIG. 5C, the protrusion portion 130 is formed to protrude inward from one portion of an inside surface of the clear aligner 100 that correspond to the tooth that has to be moved inward toward the gingiva.

When the patient wears the clear aligner 100, the protrusion portion 130 applies pressure to the tooth 51 inward toward gingiva. Thus, the tooth 51 is gradually moved into the gingiva.

FIGS. 6 to 9 are conceptual diagrams each of which illustrates that the tooth is aligned using the protrusion portion 130 that is formed to protrude inward from another portion of the inside surface of the clear aligner 100.

The fourth module can form the protrusion portion 130 that protrudes toward a tooth that needs alignment, from the inside surface of the 3D clear aligner 100, in such a manner that pressure is applied to the tooth in an intended direction.

Figure 6:
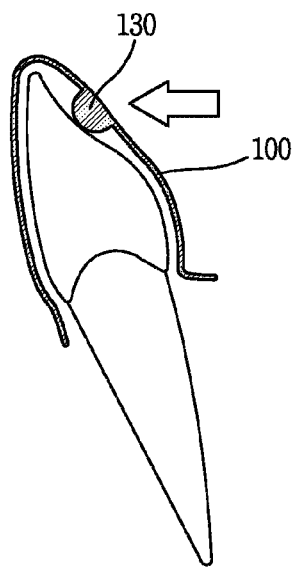
FIGS. 6 to 9 are conceptual diagrams each of which illustrates that the tooth is aligned using the protrusion portion that is formed to protrude inward from another portion of an inside surface of the clear aligner.

Referring to FIG. 6, the protrusion portion 130 can be formed to apply pressure to the tooth downward from the upper portion of the tooth. On the drawing, the protrusion portion 130 protrudes toward an upper right portion of the tooth. The protrusion portion 130 applies pressure to the tooth downward to the left. At this point, an amount of pressure varies depending on the shape of the protrusion portion 130 and the extent to which the protrusion portion 130 protrudes.

Figure 7:
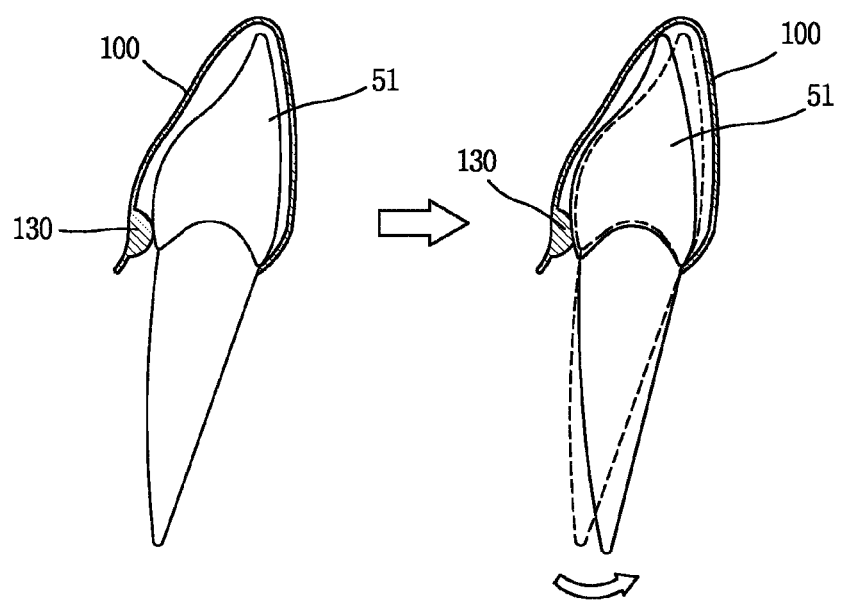

Referring to FIG. 7, on the drawing, the protrusion portion 130 is formed to protrude from the lower left portion of the inside surface of the aligner 100. The protrusion portion 130 is formed in approximately the semi-circle shape. Then, by applying pressure, the protrusion portion 130 enables the tooth 51 to rotate counterclockwise. The protrusion portion 130 serves the purpose of keeping the considerably-inclined tooth 51 in the upright position.

Figure 8:
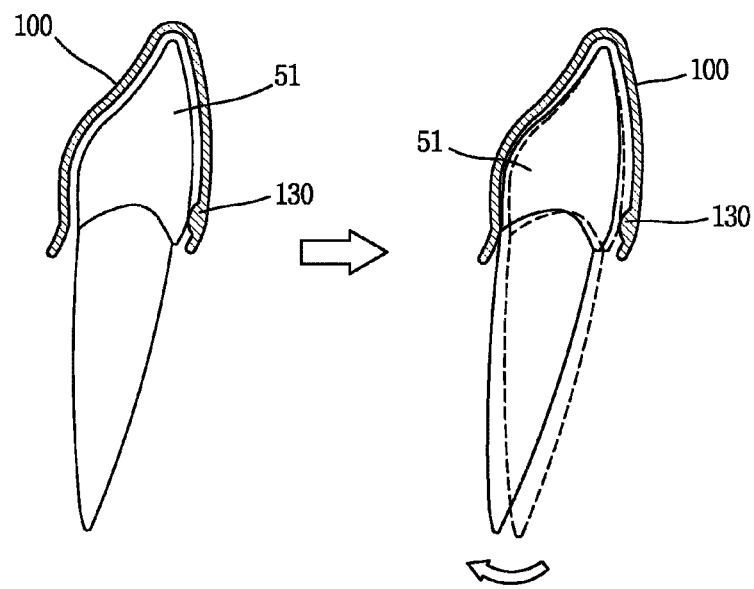

Referring to FIG. 8, on the drawing, the protrusion portion 130 is formed to protrude from the lower right portion of the inside surface of the aligner 100. Then, the protrusion portion 130 applies pressure to the tooth 51 in such a manner that the tooth 51 rotates clockwise.

In addition, in FIGS. 7 and 8, the fourth module makes can set up a center point about which the tooth rotates. In addition, the fourth module can form the protrusion portion 130 in such a manner that the tooth can rotate about the center point.

Figure 9:
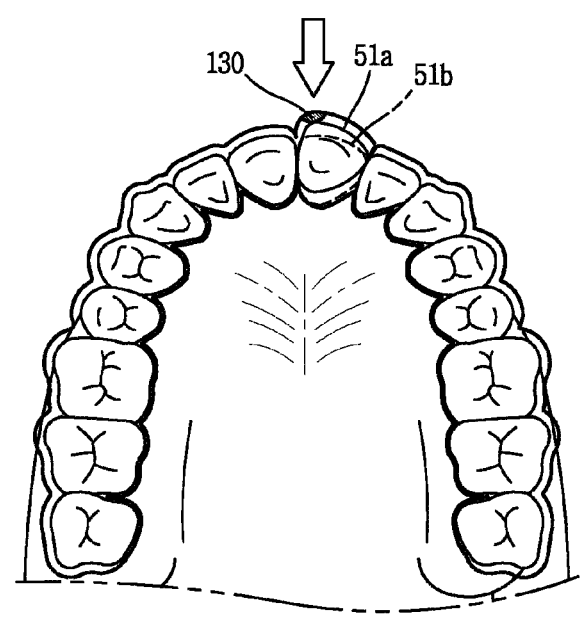

FIG. 9 illustrates the teeth in the oral cavity, which correspond to the lower jaw, when viewed from above. At this point, among the teeth that are arranged in the front portion, one tooth 51a protrudes forward. The protrusion portion 130 is formed in such a manner the protruding tooth is gradually moved inward toward the oral cavity. The post-alignment tooth 51b results from the pre-alignment tooth 51a being gradually moved inward by the protrusion portion 130.

In addition, in a case of the tooth that is positioned far inward toward the oral cavity, as opposed to the tooth that is illustrated in the drawing, the protrusion portion 130 is aligned in such a manner that the tooth is gradually moved outward from the oral cavity.

FIG. 10 is a conventional diagram illustrating the clear aligner 100 that further includes a dummy tooth in the form of an artificial teeth in an empty space between the teeth.

In a case where the 3D dental data of the patient whose tooth is extracted is available, the fourth module can form the 3D clear aligner 100 in such a manner that the 3D clear aligner 100 further includes the dummy tooth in the form of an artificial tooth that is to be implanted into the space which corresponds to the extracted tooth.

Referring to FIG. 10, there is an empty space 54 between the teeth 51.

The empty space 54 between the teeth 51 results from extracting a tooth, and so on. In such a case, when the aligner data is generated without any change in the empty space 54, the teeth adjacent to the extracted tooth, are gradually inclined or moved into the empty space 54 because there is no supporting tooth between the teeth adjacent to the extracted tooth.

The fourth module can form the 3D clear aligner 100 in such a manner that the 3D clear aligner 100 includes a dummy tooth 150 in the form of the artificial tooth which occupies the empty space in the same manner as the artificial tooth is to occupy the empty space between the teeth within the aligner. Thus, the teeth 51 are supported by the dummy tooth 150 in the form of the artificial tooth without being gradually moved or inclined to the empty space.

FIG. 11 illustrates the groove portion 120 that is formed in an upper portion of the empty space for the artificial tooth in such a manner that a position of a portion of the gingiva into which the artificial tooth is implanted is guided for an operation for implant.

The groove portion 120 is formed in the upper portion of the empty space for the artificial tooth in such a manner that a virtual position of an artificial implant tooth is guided.

FIG. 11 illustrates that the groove portion 120 is formed in the empty space 54 for the artificial tooth in such a manner as to correspond to the shape of the artificial tooth. Thus, the aligner provides guidance in implanting the artificial tooth in the empty space 54 and so on. The operation for implant and the like takes place in the inside of the groove portion 120 in the aligner.

In addition, data on markings and the like for the operation for implant is included in the aligner data on the empty space 54 in order to form the groove portion 120.

Effects that are achieved according to the present invention are as follows.

According to at least one of the embodiments of the present invention, the clear aligner data is generated based on the dental data. Material is less used than when the aligner is manufactured using a plaster cast in the related art.

In addition, according to at least one of the embodiments of the present invention, an amount of alignment can be adjusted by adjusting the thickness of the clear aligner.

In addition, according to at least one of the embodiments of the present invention, additional adjustment that uses the elastic member is possible by forming the button members on and the groove portion in the clear aligner.

In addition, the clear aligner data is stored for later use and thus the same clear aligner as the existing clear aligner can be manufactured.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

The invention claimed is:

1. A non-transitory computer readable medium having computer executable instructions thereon, wherein the instructions perform a method of generating data on a clear aligner, based on 3D data that contains data on a current arrangement of patient's teeth and on a gingiva internal structure, the method comprising:
   receiving data on a current dental state from a scanning apparatus that scans patient's teeth;
   generating 3D data on a state of the patient's teeth and of the vicinity of the patient's teeth based on data that results from the scanning;
   generating data relating to a 3D clear aligner with a predetermined thickness;
   processing the data relating to the 3D clear aligner in such a manner that at least one of a shape and a feature of the 3D clear aligner is changed, wherein processing the data comprises forming a groove portion of the 3D clear aligner, wherein the groove portion has an opening, and wherein processing the data comprises forming a button member onto which an elastic member applying pressure to a tooth is locked by passing through the opening of the groove portion, in such a manner that the tooth is gradually moved into a gingiva or is gradually moved out of the gingiva; and
   transmitting the processed data on the 3D clear aligner to an aligner manufacturing apparatus.

2. The computer readable medium of claim 1, wherein generating data further comprises adjusting a thickness attribute among attributes of the data on the 3D clear aligner.

3. The computer readable medium of claim 2, wherein generating data further comprises partially adjusting the thicknesses of the 3D clear aligner in a database in correspondence to teeth that are expressed in the 3D dental data, respectively.

4. The computer readable medium of claim 1, wherein the groove is formed in an empty space to guide a virtual position of an artificial implant tooth.

5. The computer readable medium of claim 1, wherein processing the data comprises forming a protrusion portion that protrudes toward a tooth that needs alignment, from an inside surface of the 3D clear aligner, in such a manner that pressure is applied to the tooth in an intended direction and an amount of the pressure varies depending on the shape of the protrusion portion and the extent to which the protrusion portion protrudes.

6. The computer readable medium of claim 1, wherein processing the data comprises forming the 3D clear aligner, in such a manner that the 3D clear aligner is positioned a given distance away from the 3D tooth so that a space into which medical stuff is introduced is formed in the 3D clear aligner.

7. The computer readable medium of claim 1, wherein processing the data comprises forming the 3D clear aligner in such a manner that the 3D clear aligner has multiple layers that are laminated on each other.

8. The computer readable medium of claim 7, wherein the multiples includes a first layer and a second layer, and
wherein the first layer is formed to cover the 3D teeth, and the second layer, which has a different color than the first layer, is formed to cover the first layer and to be subject to wear due to an external force.

9. The computer readable medium of claim 1, wherein processing the data comprises forming a 3D clear aligner that corresponds to an above-teeth portion of a patient's upper jaw and a 3D clear aligner that corresponds to a below-teeth portion of the patient's lower jaw, in such a manner that the 3D clear aligner that corresponds to the below-teeth portion is greater in thickness than the 3D clear aligner that corresponds to the above-teeth portion to serve as a splinter.

10. The computer readable medium of claim 1, wherein processing the data comprises forming at least one portion of the 3D clear aligner that is made of different material.

11. The computer readable medium of claim 1, wherein processing the data comprises indicating an image or a character on the 3D clear aligner.

12. The computer readable medium of claim 1, wherein the aligner manufacturing apparatus is a 3D printer.

\* \* \* \* \*